(12) United States Patent
Suzuki (10) Patent No.: US 8,980,849 B2
(45) Date of Patent: Mar. 17, 2015

(54) COMPOSITIONS AND METHODS FOR TREATING PULMONARY HYPERTENSION

(75) Inventor: Yuichiro Suzuki, Rockville, MD (US)

(73) Assignee: Georgetown University, Washington, DC (US)

( * ) Notice: Subject to any disclaimer, the term of this patent is extended or adjusted under 35 U.S.C. 154(b) by 21 days.

(21) Appl. No.: 13/641,693

(22) PCT Filed: Apr. 15, 2011

(86) PCT No.: PCT/US2011/032646
§ 371 (c)(1),
(2), (4) Date: Jan. 29, 2013

(87) PCT Pub. No.: WO2011/130605
PCT Pub. Date: Oct. 20, 2011

(65) Prior Publication Data
US 2013/0131002 A1    May 23, 2013

Related U.S. Application Data

(60) Provisional application No. 61/324,954, filed on Apr. 16, 2010.

(51) Int. Cl.
*A61K 31/70* (2006.01)
*A61K 31/704* (2006.01)
*A61K 31/496* (2006.01)
*A61K 31/7042* (2006.01)
*A61K 45/06* (2006.01)
*A61K 31/428* (2006.01)

(52) U.S. Cl.
CPC ............. *A61K 31/704* (2013.01); *A61K 31/496* (2013.01); *A61K 31/7042* (2013.01); *A61K 45/06* (2013.01); *A61K 31/428* (2013.01)
USPC ........................................................... 514/34

(58) Field of Classification Search
CPC .................................................... A61K 31/704
USPC ........................................................... 514/34
See application file for complete search history.

(56) References Cited

U.S. PATENT DOCUMENTS 7,264,803 B2 * 9/2007 Schwarz .................... 424/130.1

* cited by examiner

*Primary Examiner* — Elli Peselev
(74) *Attorney, Agent, or Firm* — Morgan Lewis & Bockius LLP (57) ABSTRACT

The present invention relates to methods of treating pulmonary hypertension in a subject including administering to the subject a therapeutically effective dose of at least one anthracycline.

18 Claims, 8 Drawing Sheets

Fig. 3A (animals with pulmonary hypertension)

Figure 5

DNR at 2 mg/kg significantly reduces thickened pulmonary smooth muscle mass induced by treating rats with chronic hypoxia

* Denotes significant difference from each other at P<0.05.

COMPOSITIONS AND METHODS FOR TREATING PULMONARY HYPERTENSION

CROSS-REFERENCE TO RELATED APPLICATIONS

This application claims priority to U.S. Provisional Application No. 61/324,954, filed 16 Apr. 2010, which is incorporated by reference herein.

STATEMENT REGARDING FEDERALLY SPONSORED RESEARCH OR DEVELOPMENT

Part of the work performed during development of this invention utilized U.S. Government funds from the National Institutes of Health, grant number RO1 HL72844. The U.S. Government has certain rights in this invention.

BACKGROUND OF THE INVENTION

1. Field of the Invention

The present invention relates to methods of treating pulmonary hypertension in a subject comprising administering to the subject a therapeutically effective dose of at least one anthracycline.

2. Background of the Invention

Pulmonary hypertension is a devastating disease without cure. The mean survival of patients with pulmonary hypertension is only a few years. The major problem of this disease is the progressive thickening of pulmonary vascular walls due to abnormal increase in the number of vascular cells, including pulmonary artery smooth muscle cells. The thickened vascular wall results in reduced lumen size, thus increasing pulmonary vascular resistance and placing a strain on the right heart ventricle, ultimately leading to right heart failure. The currently approved drugs are largely vasodilators, and their actions on the structure of the pulmonary vascular wall are limited. Furthermore, by the time patients are diagnosed as having pulmonary hypertension, vascular wall thickening has already developed. Thus, regressing thickened pulmonary vascular wall by eliminating excess vascular cells could be a better strategy to treat and possibly cure pulmonary hypertension than using vasodilators.

SUMMARY OF THE INVENTION

The present invention relates to methods of treating pulmonary hypertension in a subject comprising administering to the subject a therapeutically effective dose of at least one anthracycline. In one embodiment, the subject is identified as having pulmonary hypertension prior to administration of at least one anthracycline.

BRIEF DESCRIPTION OF THE DRAWINGS

FIG. 1 depicts in vivo treatment of rats with chronic hypoxia promoting pulmonary hypertension and pulmonary vascular thickening. Adult Sprague-Dawley rats were subjected to chronic sustained hypoxia at 10% $O_2$ in OxyCycler Oxygen Profiling System for durations indicated. (A) Right ventricle (RV) mass/[left ventricle (LV) mass+septum mass (S)] values were measured as indication of the occurrence of pulmonary hypertension and resultant right ventricular hypertrophy. (B) Rats were anesthetized and ventilated and right ventricular (RV) pressure was monitored by inserting a Millar catheter connected to PowerLab. A representative trace of RV pressure data is shown. The bar graph represents means±SEM of RV systolic pressure (RVSP) in normoxia controls and hypoxia-treated rats. (C) Hematoxylin and eosin stain shows thickened pulmonary artery smooth muscle in rats subjected to chronic hypoxia. Symbols * denote values significantly different from normoxia control (0 days).

FIG. 2 depicts daunorubicin (DNR) reduced thickening of pulmonary vascular walls in intact animals. Sprague-Dawley rats were subjected to chronic hypoxia at 10% oxygen for 2 weeks, injected with DNR in saline or saline only. Rats were then placed back in the hypoxia chamber for 3 additional days. Lungs were harvested and subjected to H&E stain. (A) Representative data is shown. (B) Bar graph shows mean values with statistical significance at P<0.05 indicated between saline and DNR treated animals with hypoxia-induced pulmonary hypertension.

FIG. 3 depicts daunorubicin (DNR) induction of apoptosis in pulmonary vascular walls in intact animals. Sprague-Dawley rats were subjected to chronic hypoxia at 10% oxygen for 2 weeks, injected with DNR in saline or saline only. Rats were then placed back in the hypoxia chamber for 3 additional days. Lungs were harvested and subjected to TUNEL assay which detects apoptotic cells (brown cells indicate TUNEL staining; some are indicated by arrows). (A) representative data from 3 groups of animals with pulmonary hypertension. (B) representative data from 3 groups of animals without pulmonary hypertension.

DETAILED DESCRIPTION OF THE INVENTION

The present invention relates to methods of treating pulmonary hypertension in a subject comprising administering to the subject a therapeutically effective dose of at least one anthracycline. In one embodiment, the subject is identified as having pulmonary hypertension prior to administration of the at least one anthracycline.

As used herein, the term a "treatment" is used to indicate a procedure which is designed ameliorate one or more causes, symptoms, or untoward effects of pulmonary hypertension in a subject. Likewise, the term "treat" is used to indicate performing a treatment. The treatment can, but need not, cure the subject, i.e., remove the cause(s), or remove entirely the symptom(s) and/or untoward effect(s) of pulmonary hypertension in the subject. The treatment can also slow the progression of or the worsening of pulmonary hypertension. Thus, a treatment may include treating a subject to attenuate symptoms such as, but not limited to, chest pain, dizziness, fainting, fatigue, leg swelling, light-headedness (especially during exercise), shortness of breath during activity and general weakness or it may include removing, decreasing the severity of the root cause or inhibiting the progression of pulmonary hypertension in the subject. Treatment of pulmonary hypertension also includes treating after-arising symptoms that are related to the onset of pulmonary hypertension, such as chest pain, dizziness, fainting, fatigue, leg swelling, light-headedness (especially during exercise), shortness of breath during activity and general weakness. As used herein, the term "subject" is used interchangeably with the term "patient," and is used to mean an animal, in particular a mammal, and even more particularly a non-human or human primate.

As used herein "pulmonary hypertension" refers to elevated blood pressure in the pulmonary circulation. Pulmonary hypertension can be either primary or secondary to pulmonary or cardiac disease. Typically, the pulmonary blood pressure in humans suffering from pulmonary hypertension is greater than about 30 mm Hg systolic and greater than about 12 mm Hg diastolic, or a mean pulmonary artery pressure in excess of about 25 mm Hg. The exact measurement of pulmonary hypertension can vary from patient to patient. Measuring pulmonary blood pressure is just one example of a method of identifying a subject as having pulmonary hypertension prior to the administration of at least one anthracycline. Other means of assessing the existence of pulmonary hypertension may include but are not limited to cardiac catheterization, chest x-ray, CT scan (chest), echocardiogram, electrocardiography, nuclear lung scan, pulmonary arteriogram and pulmonary function tests. The invention is not limited by the methods or ways of determining or assessing pulmonary hypertension in a subject. As used herein, a subject having pulmonary hypertension is a subject in need of treatment of pulmonary hypertension. In one embodiment, the subject in need of treatment of pulmonary hypertension does not have any known cancer or precancerous conditions.

As used herein "primary pulmonary hypertension" refers to pulmonary hypertension not caused by another underlying disease, whereas "secondary pulmonary hypertension" refers to pulmonary hypertension resulting from another underlying disease. Typically, the underlying disease causing secondary pulmonary hypertension is a pulmonary or cardiac disease.

Methods of treating or preventing pulmonary hypertension comprise administering a pharmaceutically effective amount of at least one anthracycline to a subject. In one embodiment, the subject is in need of treatment of pulmonary hypertension and has been identified as such prior to the administration of the at least one anthracycline. As used herein, the term "administer" and "administering" are used to mean introducing a therapeutic substance into the subject. When administration is for the purpose of treatment, the substance is provided at, or after the onset of, at least one symptom or indication of pulmonary hypertension. The therapeutic administration of a substance serves to attenuate any symptom, or prevent additional symptoms or causative events from arising. As used herein, pulmonary hypertension may or may not be perceived by the subject or clinician without further diagnosis or testing. When administration is for the purposes of preventing or reducing the likelihood of developing pulmonary hypertension ("prophylactic administration"), the substance is provided in advance of any symptom or indication of pulmonary hypertension. The prophylactic administration of the substance serves to attenuate subsequently arising symptoms or causative events or prevent or reduce the likelihood of the symptoms or causative events from arising altogether.

Anthracyclines are well known in the art. Examples of anthracyclines include but are not limited to daunorubicin, doxorubicin, epirubicin, idarubicin, pyrromycin, aclacinomycin, isorhodomycine and carminomycine.

Furthermore, the methods of treating or preventing pulomonary hypertension of the present invention also relate to coadministering one or more substances. The term "coadminister" indicates that each of at least two compounds are administered during a time frame wherein the respective periods of biological activity or effects overlap. Thus, the term includes sequential as well as coextensive administration of compounds. And similar to administering compounds, coadministration of more than one substance can be for therapeutic and/or prophylactic purposes. If more than one substance or compound is coadministered, the routes of administration of the two or more substances need not be the same. The scope of the invention is not limited by the identity of the substance which may be coadministered with the anthracycline. For example, an anthracycline may be coadministered with at least one additional pharmaceutically active substance, such as, but not limited to a cardioprotectant, a vasodilator, an iron chelator and/or a p53 inhibitor. Alternatively, an anthracycline may be coadministered with fluids or other substances that are capable of alleviating, attenuating, preventing or removing symptoms in a subject suffering from or exhibiting the symptoms of, or at risk of suffering from, pulmonary hypertension.

The terms vasodilator is readily understood in the art as a compound that cause dilation of blood vessels. Examples of vasodilators are well known in the art and include but are not limited to Hydralazine (Apresoline), Diazoxide, Minoxidil (Loniten), Sodium Nitroprusside, Nitroprusside, Diazozide, Ifenprodil Tartrate, Dilazep Dihydrochloride, Cilostazol, Dipyridamole, Isosorbide Dinitrate, Isosorbide Mononitrate, Nitroglycerin, Sildenafil, vardenafil, tadalafil (Clalis), alprostadil and Papaverine.

As used herein "vasodilation" refers to a physical change in a blood vessel, which results in an increased blood flow capacity through the blood vessel. Vasodilation can either be active vasodilation or passive vasodilation. Active vasodilation is caused by a decrease in the tonus of smooth muscle in the wall of the vessel, whereas passive vasodilation is caused by increased pressure from within the lumen of the vessel.

The term iron chelator is readily understood in the art as a chelator that forms a complex with iron. Examples of iron chelators are well known in the art and include but are not limited to deferoxamine, 2,2' bipyridine, deferiprone and desferrioxamine.

The term cardioprotectant is readily understood in the art as a compound that protects cardiac muscle tissue from damage or toxicity. Examples of cardioprotectants are well known in the art and include but are not limited to dexrazoxane, nicorandil, aprikalim and pinacidil.

The term p53 inhibitor is readily understood in the art as a compound that inhibits the function, expression or signaling of the p53 molecule in a cell. Examples of p53 inhibitors include but are not limited to pifithrin-α and those disclosed in U.S. Pat. No. 7,012,087, which is incorporated by reference.

Other compounds that can be co-administered include endothelin receptor antagonists, such as bosentan, sitaxentan, ambrisentan, and prostaglandins such as epoprostenol, treprostinil, iloprost, beraprost.

As used herein and unless otherwise indicated, the phrase "therapeutically effective amount" (or "pharmaceutically effective amount") is measured by the therapeutic effectiveness of the substance. In one embodiment, the term "therapeutically effective amount" means an amount of a substance that is sufficient to provide the desired local or systemic effect and performance at a reasonable benefit/risk ratio attending any medical treatment. The response to the therapeutically effective amount may be a cellular, organ or tissue-specific response, or system or systemic response. In one embodiment, the phrase "therapeutically effective amount" of an administered substance is measured by the therapeutic effectiveness of the substance to alleviate at least one symptom associated with pulmonary hypertension. The novelty in the invention herein is the use of anthracyclines to reduce pulmonary hypertension and it is well within the ability of one of skill in the art to determine the therapeutically effective dose of the anthracycline based on the benefit/risk analysis, i.e., to determine the therapeutic window, for each individual anthracycline. For example, one of skill in the art may determine that the antrhacycline daunorubicin may be effective at doses lower that 20 mg/kg without causing significant toxicity issues. In one embodiment, the anthracycline is administered in a dose of about 20 mg/kg or less. In another embodiment, the anthracycline is administered in a dose of about 18 mg/kg or less, 16 mg/kg or less, 14 mg/kg or less, 12 mg/kg or less, 10 mg/kg or less, 8 mg/kg or less, 6 mg/kg or less, 4 mg/kg or less, 2 mg/kg or less, 1 mg/kg or less, 0.5 mg/kg or less, or even 0.1 mg/kg or less.

A medicament comprising a substance of the present invention may be prepared by standard pharmaceutical techniques known in the art, depending upon the mode of administration and the particular disease to be treated. The medicament will usually be supplied as part of a sterile, pharmaceutical composition which will normally include a pharmaceutically acceptable carrier. This pharmaceutical composition may be in any suitable form, (depending upon the desired method of administering it to a subject). It may be provided in unit dosage form, and will generally be provided in a sealed container and may be provided as part of a kit, which may include instructions for use and/or a plurality of unit dosage forms.

The pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. Specific examples of excipients include but are not limited to poly-ethylene glycol (PEG), dimethyl sulfoxide (DMSO), ethanol and mixtures thereof. For the preparation of suspensions oils (e.g. vegetable oils) may be used to provide oil-in-water or water in oil suspensions. In certain situations, delayed release preparations may be advantageous and compositions which can deliver, for example, an anthracycline in a delayed or controlled release manner may also be prepared. Prolonged gastric residence brings with it the problem of degradation by the enzymes present in the stomach and so enteric-coated capsules may also be prepared by standard techniques in the art where the active substance for release lower down in the gastro-intestinal tract.

Pharmaceutical compositions adapted for transdermal administration may be presented as discrete patches intended to remain in intimate contact with the epidermis of the recipient for a prolonged period of time. For example, the active ingredient may be delivered from the patch by ionophoresis as generally described in Pharmaceutical Research, 3(6):318 (1986).

Pharmaceutical compositions adapted for topical administration may be formulated as ointments, creams, suspensions, lotions, powders, solutions, pastes, gels, sprays, aerosols or oils. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. The pharmaceutical compositions may contain preserving agents, solubilising agents, stabilising agents, wetting agents, emulsifiers, sweeteners, colorants, odorants, salts (substances of the present invention may themselves be provided in the form of a pharmaceutically acceptable salt), buffers, coating agents or anti-oxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used.

The examples herein are meant to illustrate only select embodiments of the present invention and are not intended to limit the scope of the inventive subject matter described herein. Any combination of any two or more of any of the embodiments described herein are contemplated.

EXAMPLES

Example 1

All animal studies were approved by the Georgetown University Animal Care and Use Committee. Adult Sprague Dawley rats (200-250 g) were placed in specialized cages connected to the OxyCycler Oxygen Profile Controller (BioSpherix, Redfield, N.Y.) which precisely controls the oxygen and nitrogen contents. Animals were subjected to hypoxic gas (10% $O_2$, balance $N_2$). Ventilation was adjusted to remove $CO_2$ to ensure that levels did not exceed 5,000 ppm (0.5%). Normoxia control animals are subjected to the same conditions except that they were exposed to ambient $O_2$. All animals were fed normal rat chow during treatment and used in accordance with institutional guidelines.

After 2-weeks of hypoxia or normoxia treatment, animals were injected intraperitoneally with saline or daunorubicin (20 mg/kg body weight; Sigma-Aldrich, St. Louise, Mo.). After injection, animals were placed back in hypoxia or normoxia condition for 3 days.

As an indication of the development of pulmonary hypertension, right ventricular hypertrophy was estimated by calculating RV/(LV+S), where RV is the mass of right ventricle, LV is the mass of left ventricle and S is the mass of septum. Right ventricular pressure was measured by inserting a 1.4 F Millar Catheter into the right ventricle at the base of apex using PowerLab 8/30 High Performance Data Acquisition System with Chart Pro in anesthetized and ventilated animals. Pulmonary arterial wall thickening was assessed histologically in hematoxylin and eosin stained lungs. Apoptosis of pulmonary vascular cells was monitored using terminal deoxynucleotidyl transferase dUTP nick end labeling (TUNEL) method.

Comparisons between the 2 groups were analyzed using a two-tailed Student's t test, and comparisons between 3 or more groups were analyzed by ANOVA with a Student-Newman-Keuls post-hoc test. $p<0.05$ was considered to be significant.

Figure 1:
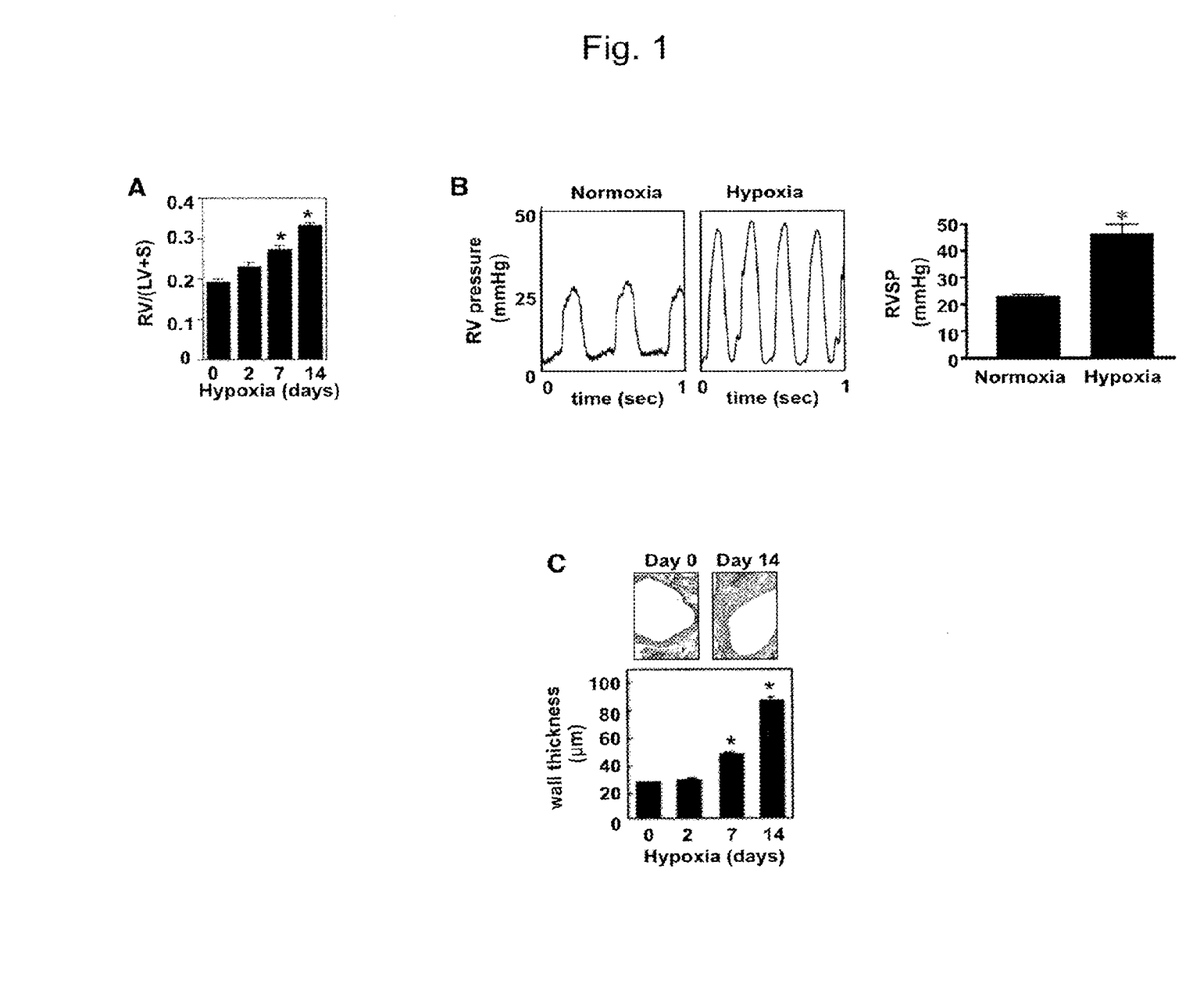

Placement of animals in the hypoxia chambers lead to the development of pulmonary hypertension as assessed by monitoring the development of right ventricular hypertrophy (FIG. 1A) and increased right ventricular pressure (FIG. 1B). Right ventricular hypertrophy and increased right ventricular pressure were also associated with pulmonary vascular wall thickening, due to increased pulmonary vascular smooth muscle cells (FIG. 1C).

Figure 2A:
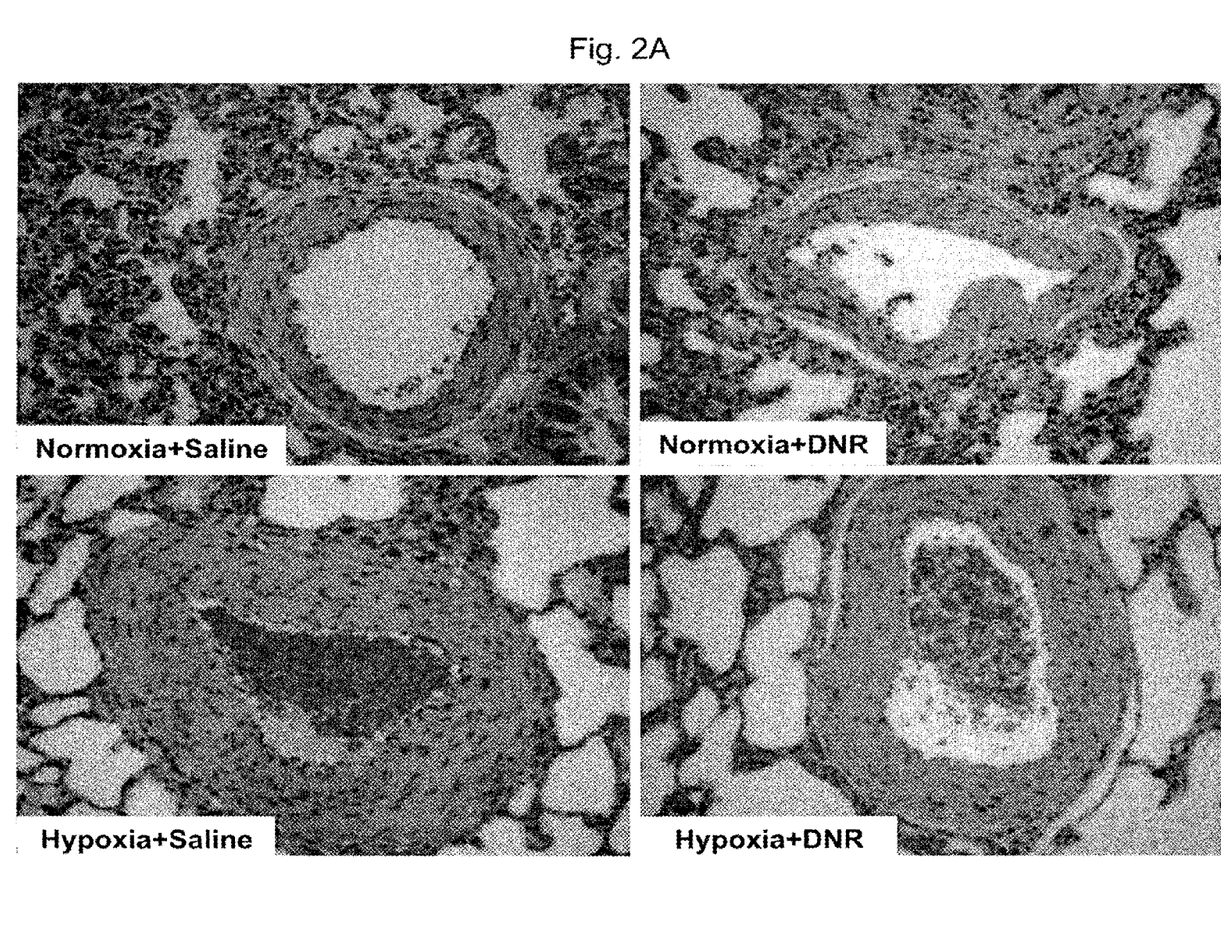
Figure 2B:
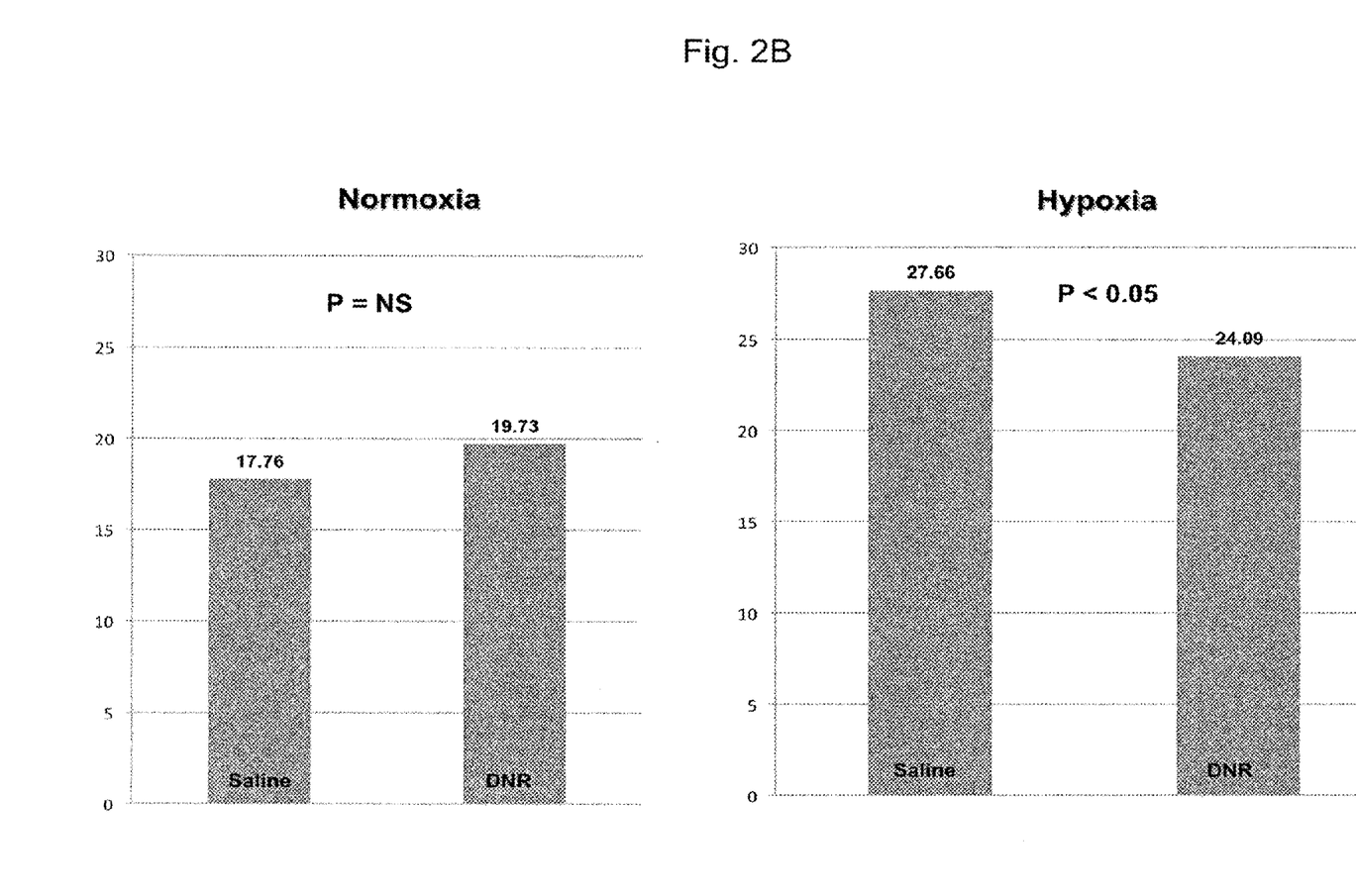

Thickened pulmonary vascular wall induced by chronic exposure to hypoxia, and daunorubicin treatment significantly reduced this hypoxia-induced wall thickening in animals with pulmonary hypertension. Surprisingly, daunorubicin treatment did not affect the thickness of the vascular walls in normal animals without pulmonary hypertension (FIG. 2).

Figure 3A:
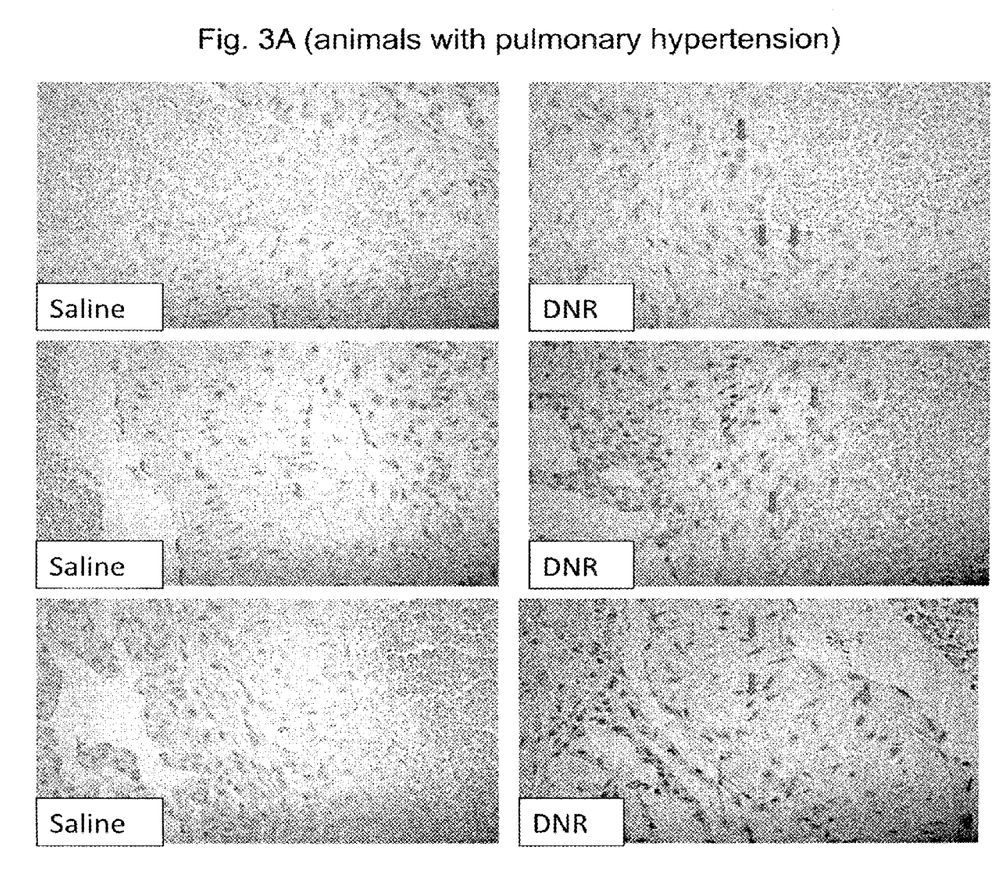
Figure 3B:
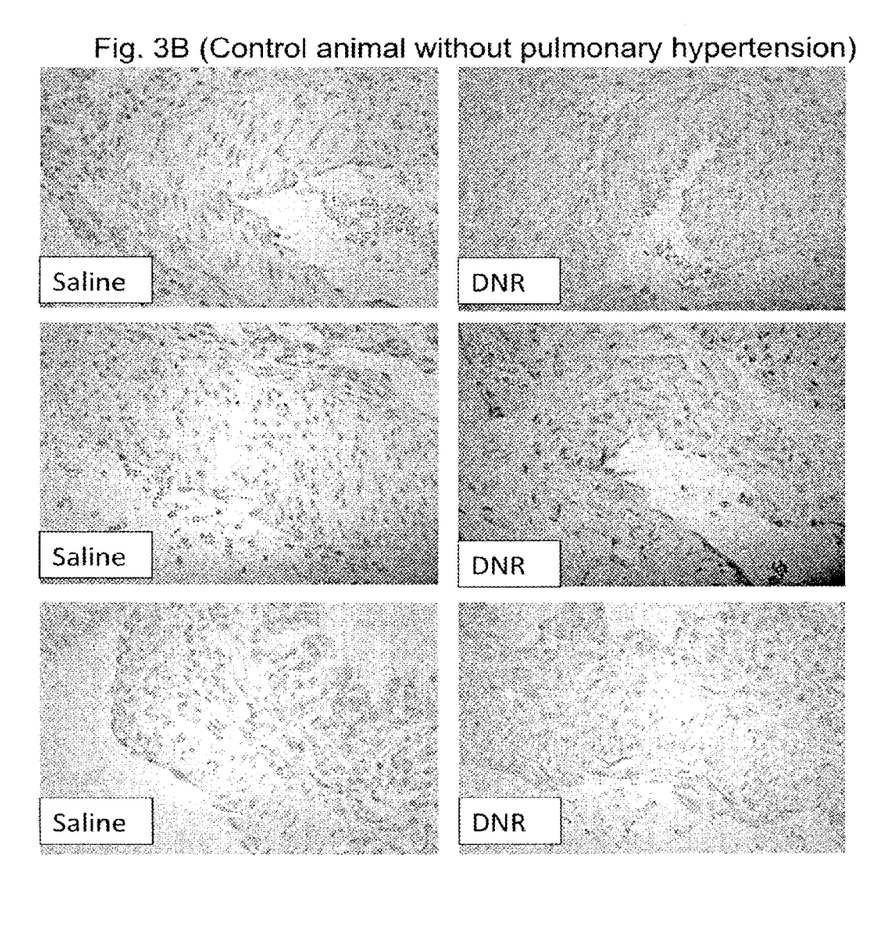

This reduction in the thickness of the cell wall in hypoxia-exposed animals was associated with induction of TUNEL positive cells, which is indicative of apoptosis. As shown in FIG. 3A, hypoxia-exposed rats treated with daunorubicin presented TUNEL-positive cells. Hypoxia-exposed rats treated with saline control did not present TUNEL positive cells. The results also demonstrate that pulmonary artery smooth muscle cells in thickened pulmonary vessels were more susceptible to induction of apoptosis than pulmonary artery smooth muscle cells in normal vessels (FIG. 3A vs. FIG. 3B). These results demonstrate that daunorubicin can selectively kill pulmonary artery smooth muscle cells involved in thickened vascular walls in subjects suffering from pulmonary hypertension, but not pulmonary artery smooth muscle cells in normal vascular walls.

Example 2

Dexrazoxane is clinically used to protect the heart against the cardiotoxic side effects of anthracyclines, such as daunorubicin. Similar to Example 1, dexrazoxane is administered (i.p.) in combination with daunorubicin in hypoxia-exposed rats and normoxic rats. Hypoxia exposure will be performed as above, and injection will also be as above, except that one additional hypoxia-exposed group is injected with daunorubicin and dexrazoxane, and another hypoxia-exposed group is injected with dexrazoxane only. After monitoring right ventricular pressure, lung and heart are processed for histological analyses to assess pulmonary vascular thickening, pulmonary vessel apoptosis and the heart histology. The 4 groups are as follows.

TABLE 1

| Group | Protocol |
| --- | --- |
| 1 | hypoxia (2 weeks) → vehicle injection → hypoxia (3 days) |
| 2 | hypoxia (2 weeks) → daunorubicin (20 mg/kg) injection → hypoxia (3 days) |
| 3 | hypoxia (2 weeks) → daunorubicin (20 mg/kg) + dexrazoxane (50 mg/kg) injection → hypoxia (3 days) |
| 4 | hypoxia (2 weeks) → dexrazoxane (50 mg/kg) injection → hypoxia (3 days) |

Daunorubicin and dexrazoxane solutions in sterile saline are injected with less than 4 µl total injection volume per g weight. Equal volume of sterile saline will be injected as a control.

As an indication of the development of pulmonary hypertension, right ventricular hypertrophy are estimated by calculating RV/(LV+S), where RV is the mass of right ventricle, LV is the mass of left ventricle and S is the mass of septum. Right ventricular pressure is measured by inserting a 1.4 F Millar Catheter into the right ventricle at the base of apex using PowerLab 8/30 High Performance Data Acquisition System with Chart Pro in anesthetized and ventilated animals. Pulmonary arterial wall thickening is assessed histologically in hematoxylin and eosin stained lungs. Apoptosis of pulmonary vascular cells is monitored using terminal deoxynucleotidyl transferase dUTP nick end labeling (TUNEL) method.

Comparisons between 2 groups is analyzed using a two-tailed Student's t test, and comparisons between 3 or more groups is analyzed by ANOVA with a Student-Newman-Keuls post-hoc test.

Example 3

This example was conducted similar to Example 1 above, except that, after 2-weeks of hypoxia or normoxia treatment, animals were injected intraperitoneally with saline or daunorubicin (2 mg/kg body weight or 5 mg/kg body weight; Sigma-Aldrich, St. Louise, Mo.).

As an indication of the development of pulmonary hypertension, right ventricular hypertrophy was estimated by calculating RV/(LV+S), where RV is the mass of right ventricle, LV is the mass of left ventricle and S is the mass of septum. Right ventricular pressure was measured by inserting a 1.4 F Millar Catheter into the right ventricle at the base of apex using PowerLab 8/30 High Performance Data Acquisition System with Chart Pro in anesthetized and ventilated animals. Pulmonary arterial wall thickening was assessed histologically in hematoxylin and eosin stained lungs. Apoptosis of pulmonary vascular cells was monitored using terminal deoxynucleotidyl transferase dUTP nick end labeling (TUNEL) method.

Comparisons between the 2 groups (2 mg/kg vs. control, or 5 mg/kg vs. control) were analyzed using a two-tailed Student's t test, and comparisons between 3 or more groups were analyzed by ANOVA with a Student-Newman-Keuls post-hoc test. $p<0.05$ was considered to be significant.

Right ventricular hypertrophy was associated with pulmonary vascular wall thickening, due to increased pulmonary vascular smooth muscle cells.

Figure 4:
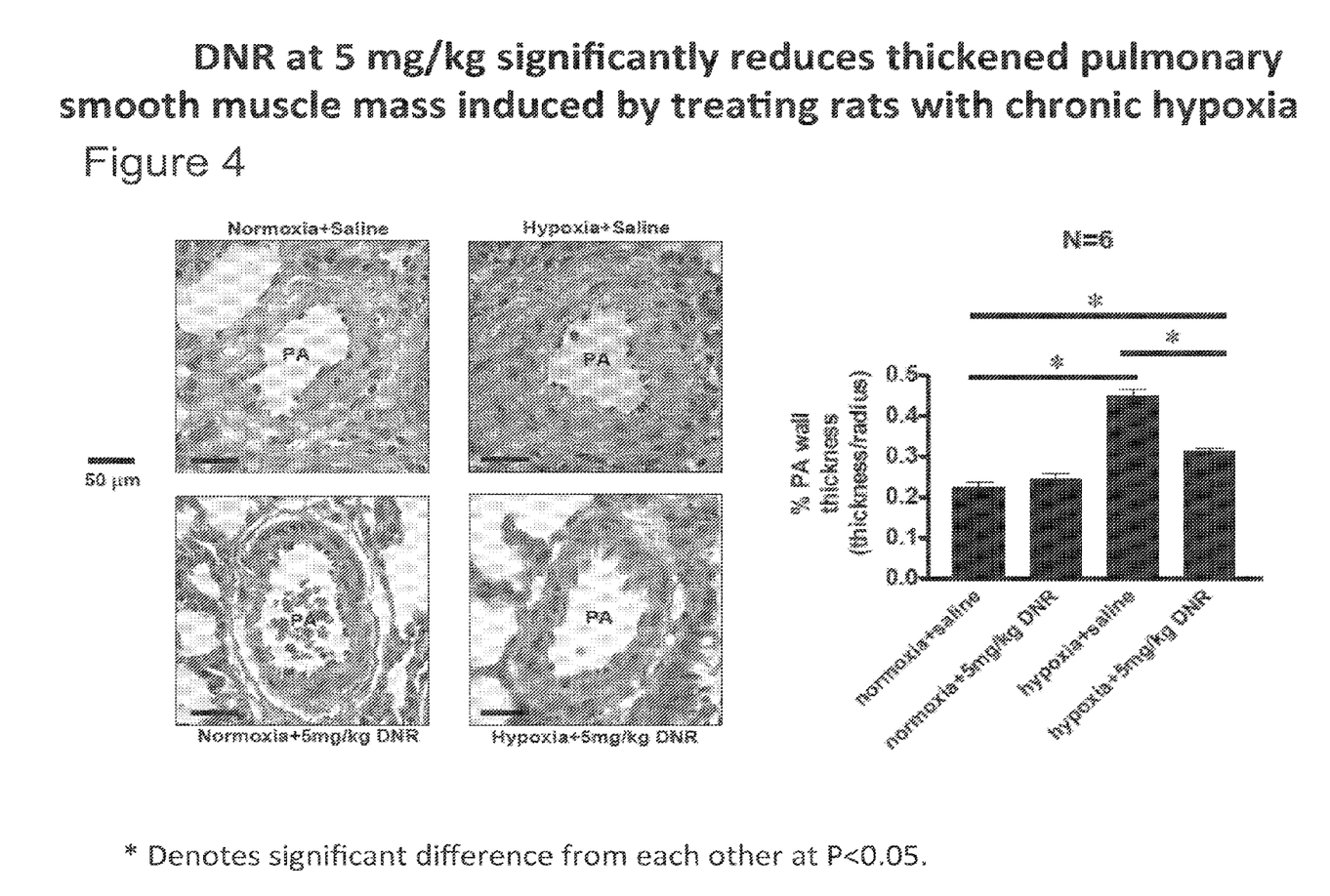
FIG. 4 depicts daunorubicin treatment (5 mg/kg) significantly reducing hypoxia-induced wall thickening in animals with pulmonary hypertension.

Daunorubicin treatment (5 mg/kg) significantly reduced hypoxia-induced wall thickening in animals with pulmonary hypertension. Surprisingly, daunorubicin treatment did not affect the thickness of the vascular walls in normal animals without pulmonary hypertension (FIG. 4).

Figure 5:
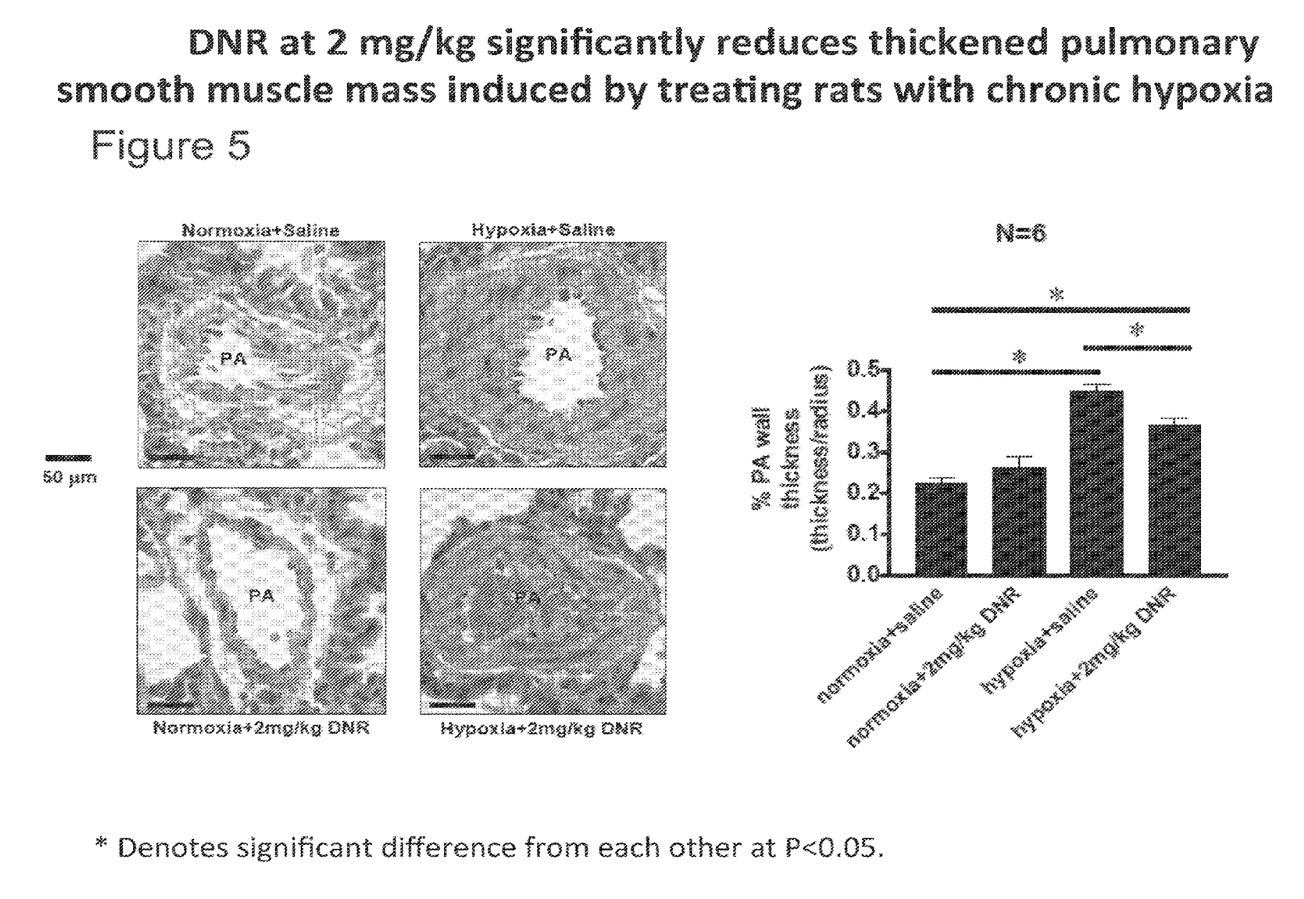
FIG. 5 depicts daunorubicin treatment (2 mg/kg) significantly reducing hypoxia-induced wall thickening in animals with pulmonary hypertension.

Daunorubicin treatment (2 mg/kg) significantly reduced hypoxia-induced wall thickening in animals with pulmonary hypertension. Surprisingly, daunorubicin treatment did not affect the thickness of the vascular walls in normal animals without pulmonary hypertension (FIG. 5).

These results demonstrate that daunorubicin can selectively kill pulmonary artery smooth muscle cells involved in thickened vascular walls in subjects suffering from pulmonary hypertension, but not pulmonary artery smooth muscle cells in normal vascular walls.

Figure 6:
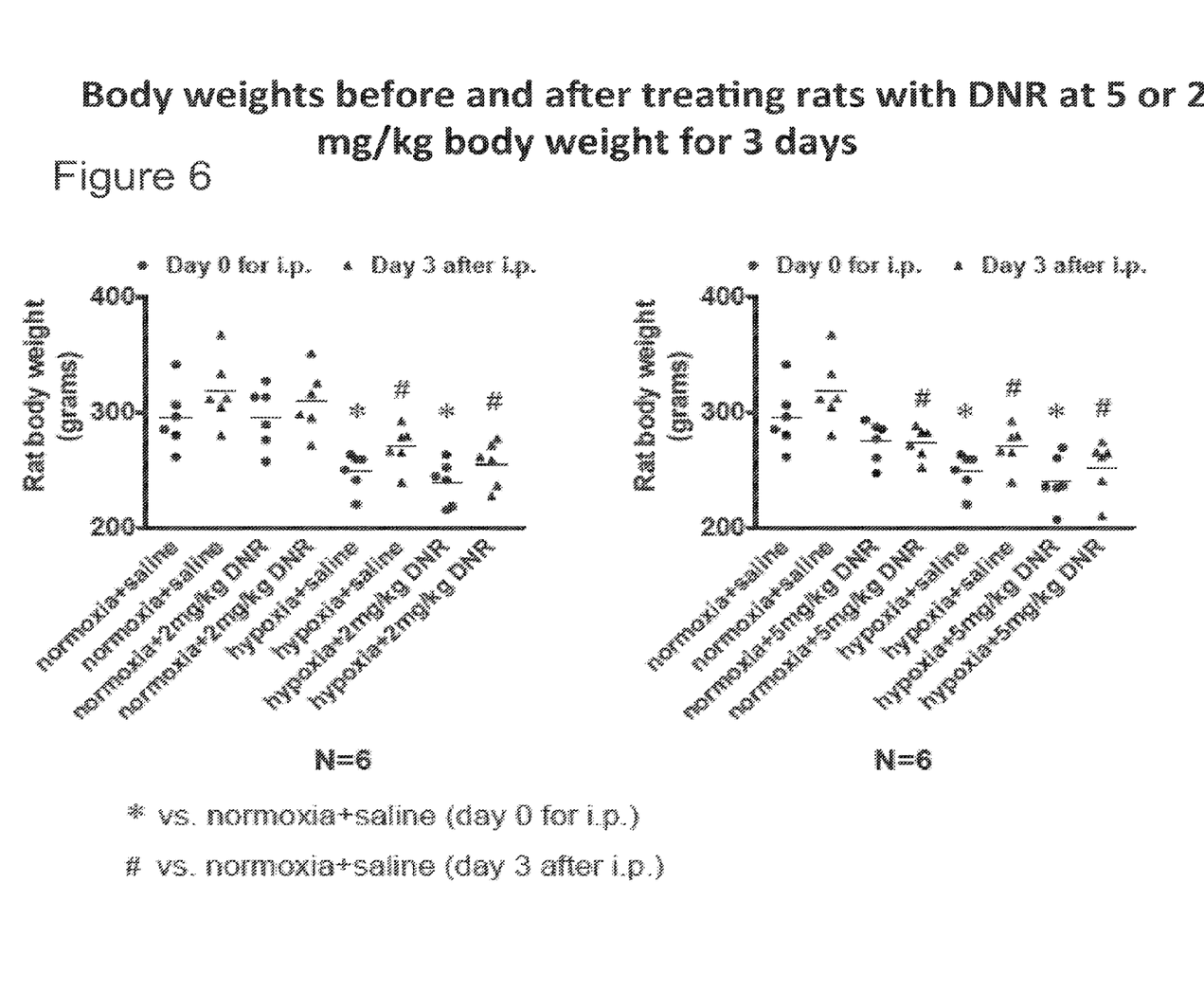
FIG. 6 depicts lower doses of daunorubicin not significantly affecting the overall body weight of animals treated.

FIG. 6 also demonstrates that these lower doses of daunorubicin do not significantly impact the overall body weight of the animals. Loss of body weight would indicate that the dose of daunorubicin might be toxic to the animals or might be causing an adverse side effect.

What is claimed is:

1. A method of ameliorating at least one cause, symptom or untowards effect of pulmonary hypertension in a subject comprising administering to the subject a therapeutically effective dose of at least one anthracycline selected from the group consisting of daunorubicin, doxorubicin, epirubicin, idarubicin, pyrromycin, aclacinomycin, isorhodomycine and carminomycine, wherein the subject was identified as having pulmonary hypertension prior to administration of the at least one anthracycline.

2. The method of claim 1, wherein the subject is a mammal.

3. The method of claim 1, wherein the subject is a human.

4. The method of claim 1, wherein the at least one anthracycline is daunorubicin or doxorubicin.

5. The method of claim 4, wherein the anthracycline is daunorubicin and the daunorubicin is administered at a dose of 20 mg/kg or less.

6. The method of claim 5, wherein the daunorubicin is administered at a dose of 10 mg/kg or less.

7. The method of claim 5, wherein the daunorubicin is administered at a dose of 5 mg/kg or less.

8. The method of claim 1, wherein the at least one anthracycline is administered via intravenous injection.

9. The method of claim 1, wherein the at least one anthracycline is administered as an inhalant.

10. The method of claim 1 further comprising co-administering a therapeutically effective amount of a cardioprotectant to the subject.

11. The method of claim 10, wherein the cardioprotectant is dexrazoxane.

12. The method of claim 1 further comprising co-administering a therapeutically effective amount of a vasodilator.

13. The method of claim 12, wherein the vasodilator is selected from the group consisting of Hydralazine, Diazoxide, Minoxidil, Sodium Nitroprusside, Nitroprusside, Diazozide, Ifenprodil Tartrate, Dilazep Dihydrochloride, Cilostazol, Dipyridamole, Isosorbide Dinitrate, Isosorbide Mononitrate, Nitroglycerin, Sildenafil, vardenafil, tadalafil, alprostadil and Papaverine.

14. The method of claim 1 further comprising co-administering a therapeutically effective amount of an iron chelator.

15. The method of claim 14, wherein the iron chelator is deferoxamine.

16. The method of claim 1 further comprising co-administering a therapeutically effective amount of a p53 inhibitor.

17. The method of claim 16, wherein the p53 inhibitor is pifithrin-α.

18. The method of claim 17, wherein the subject has a cardiovascular or pulmonary disease.

* * * * *